United States Patent [19]

Ghosh et al.

[11] Patent Number: 5,237,016
[45] Date of Patent: Aug. 17, 1993

[54] END-ATTACHMENT OF OLIGONUCLEOTIDES TO POLYACRYLAMIDE SOLID SUPPORTS FOR CAPTURE AND DETECTION OF NUCLEIC ACIDS

[75] Inventors: Soumitra S. Ghosh, San Diego; Eoin D. Fahy, La Jolla, both of Calif.

[73] Assignee: Siska Diagnostics, Inc., San Diego, Calif.

[21] Appl. No.: 293,893

[22] Filed: Jan. 5, 1989

[51] Int. Cl.[5] .................. C08F 120/56; C07H 21/02; C07H 21/04
[52] U.S. Cl. .................. 525/329.4; 525/340; 536/23.1; 536/25.4; 436/501
[58] Field of Search .................. 536/29, 27; 935/78; 435/6, 91, 810, 803; 436/501; 528/332; 526/310; 525/329.4

[56] References Cited

PUBLICATIONS

Chu et al. (1983) "Derivatization of unprotected polynucleotides", *Nucleic Acids Res.* 11: 6513–6529.
Wilcheck et al., *Biochemistry* 26, 2155 (1987).
Wilcheck et al., *PNAS* 72, 1055 (1975).
Kremsky et al., *Nucleic Acids Research* 15, 2891 (1987).
Inman, *Meth. Enzymol.* 34, 30 (1969).
Bernatowitz et al., *Anal. Biochem.* 155, 95 (1986).
Ghosh et al., *Nucl. Acids Res.* 15, 5353 (1987).
Li et al., *Nucl. Acids Res.* 15, 5275 (1987).
Chu et al., *Nucl. Acids Res.* 14, 5591 (1986).
Connolly, *Nucl. Acids Res.* 13, 4485 (1985).
Keller et al., *Helvetica Chimica Acta* 58, 531 (1975).
Kwoh et al., *Proc. Natl. Acad. Sci. USA* 86 (1989).
Goodchild, Bioconjugate Chemistry 1(3): 165–186, 1990.
Chu et al., Nucl. Acids Res. 11(18): 6513–6529, 1983.

*Primary Examiner*—Johnnie R. Brown
*Assistant Examiner*—Gary L. Kunz
*Attorney, Agent, or Firm*—Fitch, Even, Tabin & Flannery

[57] ABSTRACT

This invention concerns methods and means for covalent attachment of oligonucleotides to solid supports substantially at their 5'-ends. According to the invention thiol-oligonucleotides are attached to bromoacetyl-derivatized polyacrylamide supports, or conversely, bromoacetyl-oligonucleotides are immobilized on thiol-polyacrylamide supports.

In a further aspect, this invention relates to bromoacetyl-oligonucleotides that may be immobilized on thiol-polyacrylamide solid supports, thiol-oligonucleotides immobilized on bromoacetyl-derivatized polyacrylamide supports as well as to methods for capture of nucleic acids by oligonucleotides attached to polyacrylamide solid supports, either by direct capture or in sandwich hybridization formats.

5 Claims, 6 Drawing Sheets

DNA - 5' - OH

↓ T4 KINASE ATP

↓ $NH_2(CH_2)_6NH_2$

↓

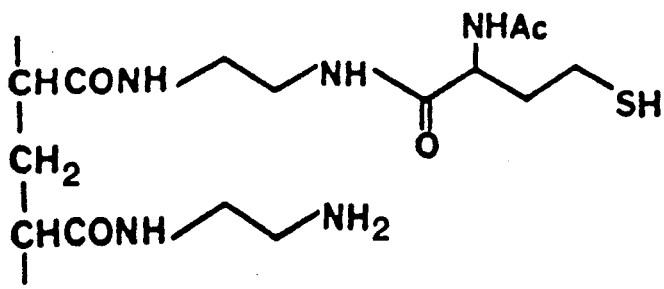
FIG. 6
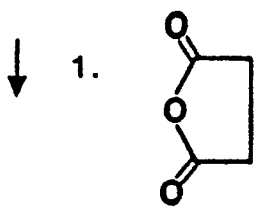
2. TRIS pH 8.5
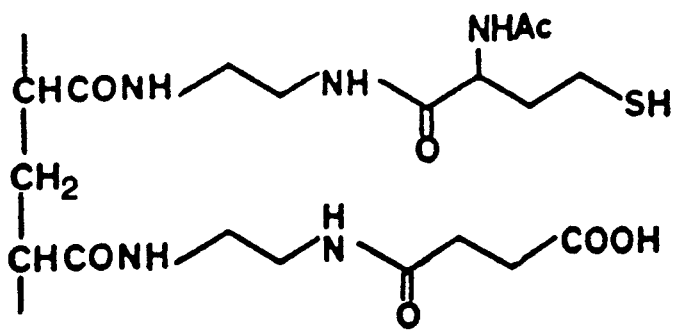
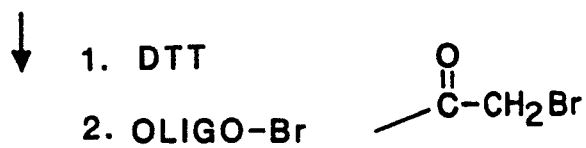
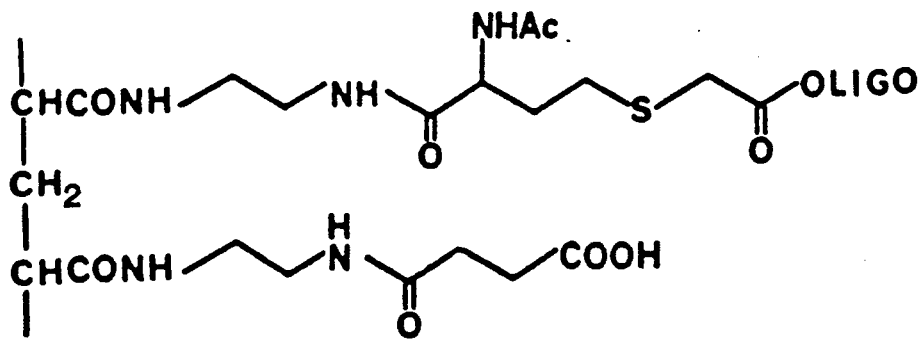

END-ATTACHMENT OF OLIGONUCLEOTIDES TO POLYACRYLAMIDE SOLID SUPPORTS FOR CAPTURE AND DETECTION OF NUCLEIC ACIDS

FIELD OF THE INVENTION

The present invention generally relates to certain developments in the chemistry of solid supports for the attachment of oligonucleotides.

More particularly, the present invention is directed to solid supports containing oligonucleotides in end-attachment, for capture and detection of nucleic acids, including single- and double-stranded DNA and RNA targets.

This invention further concerns methods and means for covalent attachment of oligonucleotides to solid supports substantially at their 5'-ends. According to the invention thiol-oligonucleotides are attached to bromoacetyl-derivatized polyacrylamide supports, or conversely, bromoacetyl-oligonucleotides are immobilized on thiol-polyacrylamide supports.

In a further aspect, this invention relates to bromoacetyl-oligonucleotides that may be immobilized on thiol-polyacrylamide solid supports, thiol-oligonucleotides immobilized on bromoacetyl-derivatized polyacrylamide supports as well as to methods for capture of nucleic acids by oligonucleotides attached to polyacrylamide solid supports, either by direct capture or in sandwich hybridization formats.

BACKGROUND OF THE INVENTION

It is often desirable to detect very small amounts of extracted or in vitro amplified nucleic acids, for example in biological samples. According to the most common approach, the target nucleic acid is hybridized to an oligonucleotide. In order to obtain a detectable signal, proportionate to the amount of the target, either the target nucleic acid or the oligonucleotide needs to be associated with a signal generating reporter element, such as a radioactive atom or a chromogenic molecule, or, an enzyme such as alkaline phosphatase. The signal generated by a properly hybridized nucleic acid can be detected and measured by methods known in the art. Many of the commonly used techniques of molecular biology require the immobilization of the targets on solid supports, to enable fractionation and identification of specific sequences. The target nucleic acid may be captured by oligonucleotides immobilized on solid supports, or more frequently, so-called "sandwich" hybridization systems are employed, using a capture oligonucleotide covalently attached to a solid support for capturing detection oligonucleotide-target nucleic acid adducts formed in solution. Typical solid supports are, for example, nitrocellulose or nylon membranes, activated agarose supports or diazotized cellulose supports. However, the bonds between these supports and the oligonucleotides are either not covalent, thereby allowing a certain release of the oligonucleotides from the support, or the supports have other shortcomings. For example, N-hydroxysuccinimide or cyanogen bromide activated polysaccharide affinity supports have a serious drawback in the leakage of ligands. This not only leads to misleading results but, even more importantly, poses health hazards when immunoaffinity-purified products produced by recombinant DNA synthesis are complexed with mouse monoclonal antibodies [see e.g. Wilchek et al., *Biochemistry* 26, 2155 (1987) and Wilchek et al. PNAS 72, 1055 (1975)]. Leakage from solid support obviously interferes with affinity purification: if the free ligand that leaks from the support is more effective as a binder than the insolubilized ligand, the free ligand will bind the target macromolecule essentially irreversibly, and prevent affinity adsorption to the column. Further, cyanogen bromide activation of polysaccharide supports leads to the formation of N-substituted isoureas on the surface of the matrix. These confer undesirable ion exchange properties to the support, which become problematic in affinity chromatography, when analytes (such as nucleic acids) are present in very minute concentrations.

The attachment of oligonucleotides containing an aldehyde or carboxylic acid group at the 5'-terminus to non-porous polystyrene latex solid microspheres is disclosed in Kremsky et al., *Nucleic Acids Research* 15, 2891 (1987). Although this method provides good end-attachment results, it is disadvantageous in that at the end of the coupling reaction, non-covalently bound oligonucleotide requires removal by a tedious gel electrophoresis step.

Therefore, solid supports with cross-linked, porous polymeric matrix structures that are able to capture and covalently bind oligonucleotides are preferred. For example Sephacryl beads are widely used due to their excellent hybridization properties.

A so called "bead-based sandwich hybridization system" (BBSHS) is, for example, described in the following publications: EP 276, 302 and Gingeras et al., *PNAS* (in press). According to this method, in a first step, a target nucleic acid and an oligonucleotide probe used for its detection, which is complementary to at least a region of the target, are hybridized. The obtained adduct is then captured by a second oligonucleotide, that is complementary to a different region of the target, and is end-attached to a solid support. The amount of the detection oligonucleotide associated with the solid support is directly related to the amount of the target captured. In this way, the BBSHS can be used to determine the amount of a single-stranded nucleic acid in a sample. In this and similar assays most commonly radioactively (e.g., $^{32}P$) labeled cloned DNAs or synthetic oligonucleotides are employed. $^{32}P$-labeled oligonucleotide probes used in conjunction with Sephacryl TM dextran beads in BBSHS experiments provide about 10:1 or better signal to noise ratios with target sequences present in about 0.5 fmole amounts.

In practice, non-radioisotopic reporter systems are often preferred, primarily due to the inconveniences associated with handling, storage and disposal of radioisotopes. Successful application of a non-radioisotopic reporter system requires a detection system which exhibits high sensitivities and low background properties when used in conjunction with the reporter system on a given solid support. The Sephacryl TM dextran beads supports show serious limitations when used in conjunction with non-radioisotopic, e.g. colorimetric, detection systems. For example, the colorimetric signal from enzyme-oligonucleotide conjugates in sandwich formats and direct capture experiments on Sephacryl TM dextran beads was compromised by undesirable background, thereby giving low signal to noise ratios. In the presence of target, the non-specific background can be a result of:

1) hybridization of the detection and capture oligonucleotide to non-exact sequences of the target nucleic acid;

2) hybridization of the detection oligonucleotide to the capture oligonucleotide;

3) non-specific attachment of the detection oligonucleotide to the bead support or walls of the reaction vessel.

While the first two of these possible causes can be minimized by sufficiently stringent solution hybridization, capture and wash conditions, the reasons for non-specific binding properties are poorly understood.

It would be desirable to find solid supports that have better binding properties, e.g. on which the non-specific attachment of the oligonucleotides used for detection of the target nucleic acids is lower and which show a greater capture potential of the immobilized probe, especially when used in conjunction with nonradioisotopic detection systems.

The properties most sought for in solid supports used for detection of nucleic acids are:

hydrophilicity ease of handling, such as compatibility with centrifugation techniques the presence of suitable functional groups low non-specific binding of the detection oligonucleotides.

In search for new solid supports, attention focused on polyacrylamide-based matrices. These supports are commercially available in a wide range of pore sizes, and are used routinely, for example, in affinity chromatography. Their hydrophilicity, lack of charged residues on their surface, and ease of derivatization are some of the properties which make them potentially attractive as supports for the attachment of oligonucleotides. Chemical derivatization of these cross-linked polyacrylamide beads for use in affinity chromatography provided spaced-out functional groups for attaching specific ligands in orientations favorable for specific binding with various macromolecules, thereby enabling the selective retention of these macromolecules, e.g., proteins [Inman, J. K., *Meth. Enzymol.* 34:30 (1974)]. Inman presented a convenient method for the preparation of hydrazide derivatives of cross-linked polyacrylamides by reacting their primary amide groups with hydrazine. Depending on the reaction conditions, hydrazide derivatives with different levels of hydrazide functionality were obtained. The hydrazide derivatives are suitable starting materials for the preparation of other derivatives. For example, bromoacetyl-derivatized polyacrylamide matrices can be obtained by reacting the hydrazide derivatives with N-hydroxysuccinimide ester of bromoacetic acid, on the analogy of the reaction described by Bernatowicz et al., *Anal. Biochem.* 155, 95 (1986).

Our further goal was to develop a methodology for the attachment of oligonucleotides to solid supports by which the nucleic acids are tethered to the solid supports by their 5'-ends. In the case of the conventionally used solid supports, e.g. Sephacryl ™ dextran beads, the degree of end-attachment is relatively low (about 50-55%; Ghosh et al., *Nucl. Acids Res.* 15:5353; (1987)). A higher degree of end-attachment would be manifested in greater capture potential of the immobilized oligonucleotide probe.

As an object of the present invention, it has been found that thiol and bromoacetyl groups of suitably derivatized oligonucleotides and polyacrylamide solid supports react with reasonable yields and their reaction, surprisingly, results in an almost 100% end-attachment of the oligonucleotides. Accordingly, thiol-derivatized oligonucleotides were used in combination with bromoacetyl-derivatized polyacrylamide solid supports. Thiol-oligonucleotides can, for example, be prepared as described by Peng Li et al., *Nucl. Acids Res.* 15, 5275 (1987) or Chu et al., *Nucl. Acids Res.* 14, 5591 (1986).

Alternatively, bromoacetyl-oligonucleotides were attached to thiol-derivatized polyacrylamide supports. Bromoacetyl-derivatized oligonucleotides are new compounds. The thiol-derivatized polyacrylamide supports are known in the art, and are, for example disclosed in *Meth. Enzymol.* 34:30 (1974). The known thiol-affinity supports were prepared by the coupling of carboxyl groups with cystamine, followed by reduction with excess DTT and not via hydrazide derivatives as in the process of the present invention.

SUMMARY OF THE INVENTION

The present invention relates to oligonucleotides immobilized on solid supports and to new methods for the attachment of oligonucleotides to solid supports.

More particularly, this invention relates to oligonucleotides immobilized on polyacrylamide solid supports and processes for coupling said oligonucleotides to said polyacrylamide supports. By developing a new methodology for the immobilization of oligonucleotides on polyacrylamide matrices, our primary goals were to investigate the influence of pore sizes on the hybridization properties of immobilized oligonucleotides, and to increase the coupling efficiency, particularly, to increase the percentage of oligonucleotides that are attached to the solid support by their 5'-termini. As hereinabove described, the experiments were performed with two essential systems. Either thiol-derivatized oligonucleotides were attached to bromoacetyl-derivatized solid supports or bromoacetyl oligonucleotides were coupled with thiol-derivatized polyacrylamide solid supports. Although coupling efficiencies varied considerably depending on the actual format used, we have surprisingly found that in both formats essentially all (more than 95%) oligonucleotides were end-attached to the polyacrylamide solid supports. This was reflected in the superior direct capture ability of the oligonucleotides immobilized according to the present invention for complementary oligonucleotides and double stranded DNAs. Polyacrylamide supports with very high (about $2 \times 10^7$ daltons) exclusion limits performed particularly well.

In another aspect of the invention, we have found that non-specific adsorption of the negatively charged nucleic acids can be considerably reduced by converting the residual functionalities of solid supports (that do not participate in the coupling reaction) into other functionalities having anionic properties, e.g. carboxylic or trinitrophenyl groups. The obtained supports with mixed functionalities are particularly preferred for practicing the present invention.

Accordingly, the present invention relates to polyacrylamide supports having covalently attached thereto oligonucleotides substantially at their 5'-ends. In another aspect, the present invention is directed to a process for coupling thiol-derivatized oligonucleotides to polyacrylamide supports substantially at their 5'-ends, the primary amide groups of said supports being at least partially converted into bromoacetyl groups prior to end-attachment.

According to another aspect, the invention relates to a process for coupling bromoacetyl-derivatized oligonucleotides to polyacrylamide supports substantially at their 5'-ends, the primary amide groups of said supports being at least partially converted into thiol groups prior to end-attachment.

Following either coupling strategy, the invention includes further derivatization of the polyacrylamide supports by converting their functionalities not involved in coupling into anionic functional groups to provide better non-specific adsorption results.

According to a further aspect, there are provided oligonucleotides derivatized at their 5'-termini with bromoacetyl groups.

According to a still further aspect, the invention concerns bromoacetyl-derivatized oligonucleotides immobilized on thiol-derivatized polyacrylamide solid supports, or conversely, thiol-derivatized oligonucleotides immobilized on bromoacetyl-derivatized polyacrylamide solid supports.

The present invention is directed to the above aspects and all associated methods and means for accomplishing such. For example, methods for preparation and purification of the detection and capture oligonucleotides, including synthesis or isolation from a natural source via restriction cleavage and subsequent purification;

preparation of oligonucleotide-signal element (e.g., radioactive atom, enzyme, fluorescent or chemiluminescent probes, mercury-based detectors, etc.) adducts for use in hybridization with the target nucleic acids;

hybridization techniques for hybridizing the target nucleic acid to the detection (and capture) oligonucleotide;

and so forth, are within the scope of this invention.

BRIEF DESCRIPTION OF THE DRAWINGS

FIG. 6 shows the acylation of thiol-derivatized Trisacryl TM polyacrylamide supports and the use of the products with mixed functionalities in capturing bromoacetyl oligonucleotides.

DETAILED DESCRIPTION OF THE INVENTION

1. Definitions and General Methods

Figure 1:
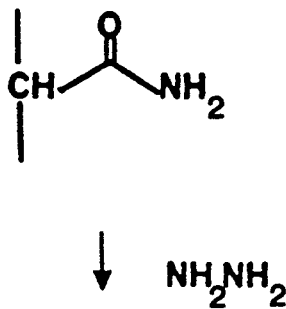
FIG. 1 illustrates the synthesis of bromoacetyl-(Reaction A) and sulfhydryl-containing (Reaction B) Bio-Gel TM polyacrylamide supports.
Figure 1:
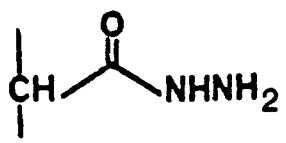
Figure 1:
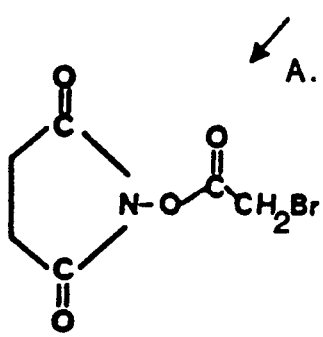
Figure 1:
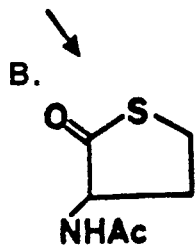
Figure 1:
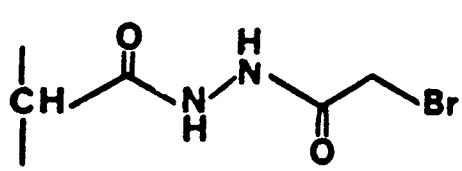
Figure 1:
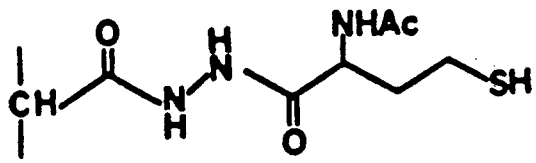

The term "oligonucleotide" as used throughout the specification and the claims refers to nucleic acids including both single and double stranded RNA and DNA molecules that may be isolated from a natural source, may be synthesized or produced by restriction digest.

By the term "detection oligonucleotide" or grammatical variations thereof is meant a nucleic acid (RNA or DNA) sequence (isolated from a natural source, synthetically produced or a product of restriction digest carrying a reporter label) that has sufficient homology with a target nucleic acid sequence such that under suitable conditions it is capable of hybridizing with said target sequence.

The term "capture oligonucleotide" specifically refers to a nucleic acid (RNA or DNA) sequence (isolated from a natural source or synthetically produced or a product of restriction digest) that is attached to a solid support, preferably substantially at its 5'-end, and that has sufficient homology with a target nucleic acid sequence (different from the sequence hybridized to the detection oligonucleotide) such that under suitable conditions it is capable of hybridizing with said target sequence.

Typical detection and capture oligonucleotides are about 12 to 200 nucleotides, preferably about 15 to 40 nucleotides in length, and usually share at least about 12 bp, preferably about 25 bp complementarity with the target nucleic acid sequence.

"Polyacrylamide supports" are cross-linked polyacrylamide matrices that are commercially available in a wide range of pore sizes. Typical representatives of such matrices are Bio-Gel TM polyacrylamide beads, manufactured by Bio-Rad (USA) that are further categorized according to their exclusion volumes. The molecular weight exclusion limits of Bio-Gel TM polyacrylamide P-2, Bio-Gel TM polyacrylamide P-10, Bio-Gel TM polyacrylamide P-60, and Bio-Gel TM polyacrylamide P-200 are 2000, 10000, 60000 and 200000 daltons, respectively. Although our experiments were predominantly carried out with Bio-Gel TM polyacrylamide beads, other polyacrylamide supports, including those in which certain groups, e.g. the amide groups are substituted, may also be used for practicing the present invention. A typical representative of such supports is Trisacryl TM polyacrylamide GF-200 (IBF Biotechnics, USA) that is produced by copolymerization of N-acryloyl-2-amino-2-hydroxymethyl-1,3-propane diol and has an exclusion limit of $2 \times 10^7$ daltons. In this resin the secondary amides contain 2-hydroxymethyl-1,3-propane diol substituents, each of its repeating units containing three hydroxymethyl groups and one secondary amide group. Consequently, this polymer is more hydrophilic in character than the Bio-Gel TM polyacrylamide resins.

The primary amide groups of the polyacrylamide supports used according to the present invention are at least partially converted into bromoacetyl groups or thiol groups prior to the attachment to the oligonucleotides. The bromoacetyl and thiol derivatives were generated from hydrazide-derivatized supports. Further details of the respective procedures are to be found in the description of preferred embodiment and in the examples.

Since the conversion of hydrazide supports into bromoacetyl or thiol derivatives is not quantitative, the unconverted hydrazide functionalities are available for further derivatization; thus, if desired, they can be further converted into other groups, such as carboxyl, trinitrophenol, etc., groups. All of such derivatives are within the scope of the present invention. It should be noted that, although the bromoacetyl and thiol-derivatized polyacrylamide supports were prepared from the respective hydrazide compounds, other synthetic routes may also be available and are encompassed by the invention, provided that they are suitable for the production of polyacrylamide supports the primary amide groups of which are at least partially converted into bromoacetyl or thiol groups (see e.g. Inman, *Meth. Enzymol.* 34, 30 (1974)).

Oligonucleotides can be synthesized and purified by any method known in the art, for example using the solid-phase cyanoethyl phosphoramidite method and HPLC purification [Ghosh, et al., *Nucl. Acids Res.* 15, 5353 (1987)]. Alternatively, they can be isolated from natural sources or produced synthetically or by restriction enzyme cleavage and, if desired, tailored so as to be suitable for the intended use.

Thiol- and bromoacetyl-derivatized oligonucleotides can be prepared, as hereinbefore described, by literature-known processes. Further details of their preparation are given in the description of preferred embodiments of the invention and in the examples.

In the specification and claims, when describing the process of hybridization between oligonucleotides and solid supports, the terms "attachment", "coupling", "tether", "binding" and "immobilization" are used interchangeably and refer to covalent linkage of oligonucleotides to the solid supports.

The term "TAS" is used to refer to the transcription amplification system disclosed in the copending U.S. Ser. No. 07/202,978 (now abandoned) that is a continuing application of U.S. Ser. No. 07/064,141 (now abandoned). This method involves using oligonucleotides to prime the synthesis of a double-stranded DNA copy (cDNA) of the target DNA or RNA sequence.

In an embodiment of TAS, one of the oligonucleotides, primer A contains, within its sequence, the T7 RNA polymerase promoter binding sequence (PBS) attached to sequences complementary to the target sequence (TCS). Elongation from this primer by reverse transcriptase results in the generation of a single-stranded cDNA containing the T7 promoter at its 5' end. A second primer oligonucleotide, primer B, is complementary to the first cDNA strand at some distance (100–300 bases) downstream of primer A. Primer B is used to initiate synthesis of the second cDNA strand, producing a double-stranded cDNA with the T7 RNA polymerase promoter attached. Incubation of the double-stranded cDNA with T7 RNA polymerase and ribonucleotide triphosphates will result in the synthesis of RNA transcripts from the cDNA. Additional amplification can be achieved by repeating TAS on the newly synthesized RNA.

As to other aspects of the invention, including preparation and purification of oligonucleotides, preparation of oligonucleotide-target nucleic acid adducts, methods for attachment of oligonucleotides to solid supports, hybridization methodologies, detection and measurement of signals generated by properly hybridized nucleic acids, etc., reference is made to standard textbooks of molecular biology.

See, for example, Maniatis, et al., *Molecular Cloning: A Laboratory Manual*, Cold Spring Harbor Laboratory, New York 1982, and the various references cited therein; Davis et al., Basic Methods in Molecular Biology, Elsevier Science Publishing, Inc., New York (1986) and Hames, et al., *"Nucleic Acid Hybridization"*, IRL Press, (1985).

2. Description of Preferred Embodiment

Before further derivatization, the polyacrylamide matrices, e.g. Bio-Gel TM polyacrylamide beads, are treated with hydrazine, essentially following the procedure of Inman, Supra. (See Reference Example 2.) Depending on the hydrazine concentrations, reaction temperatures and reaction times hydrazide supports with various substitution levels of the hydrazide functionality may be obtained. The reaction can be carried out at room temperature or at higher temperatures (see Inman Supra). Hydrazide group densities may be measured by the method given in the Analytical Procedures section of the Inman reference referred to above or Reference Example 1d. In these experiments polyacrylamide resins with different exclusion limits can be employed, the higher exclusion limits being preferred. According to a particularly preferred embodiment, polyacrylamide supports having large pore sizes, in particular those with exclusion limits over 400000 daltons, most preferably about $2 \times 10^7$ daltons, such as Trisacryl TM polyacrylamide GF 2000 (IBF Biotechnics, USA) are used.

Although the non-specific binding of [$^{32}$P]-labeled oligonucleotides was found to be low and not dependent on the level of substitution of the hydrazide functionalities on hydrazide-derivatized Bio-Gel TM polyacrylamide resins, hydrazide-derivatized supports did not perform well in binding experiments with enzyme-oligonucleotide conjugates (Ghosh, et al., *Anal. Biochem*, in press), primarily due to increased non-specific binding, principally attributed to the enzyme component of the conjugate. This problem was thought to be eliminated by further derivatization of the supports.

According to an embodiment of the invention, thiol-oligonucleotides are coupled to bromoacetyl-derivatized polyacrylamide supports.

The bromoacetyl derivatives of polyacrylamide supports are preferably obtained by treatment of the hydrazide functionalized supports with excess of bromoacetic acid-N-hydroxysuccinimide ester, essentially following the procedure described by Bernatowitz et al., Supra. The extent of derivatization can be determined by a two-step procedure. In the first step, the supports are exposed to a large excess of dithiothreitol (DTT) to effect a quantitative bromoacetyl-to-thiol functionality conversion. The thiol groups are then titrated with Ellman's reagent [5,5'-dithio-bis(2-nitrobenzoic acid)]. Under normal reaction conditions, the conversions usually range between 16–56%, therefore, the residual hydrazide groups are still available to further derivatization. Carboxyl derivatives can be obtained by treating the bromoacetyl derivatized supports with excess glutaric anhydride, to effect a hydrazide-to-carboxyl transformation.

In non-specific binding experiments with oligonucleotide-alkaline phosphatase conjugates the bromoacetyl-derivatized supports perform considerably better than the hydrazide-derivatives. Non-specific binding is further reduced by the hydrazide-to-carboxyl transformation. It was found to be advantageous to silanize the eppendorf tubes and have 1% BSA in the hybridization solutions to prevent adhesion of the oligonucleotide-enzyme conjugates to the walls of the tubes.

To effect coupling, the oligonucleotides are also derivatized. Since thiol compounds, due to their greater nucleophilicity over amines, show enhanced reactivities towards alpha-halo carbonyl substituted compounds, according to the invention, the bromoacetyl-derivatized polyacrylamide supports are coupled with thiol-oligonucleotides. Preferably, thiol-derivatized oligonucleotides are prepared using a [$^{32}$P]-labeled 5'-phosphorylated oligonucleotide in two steps: (1) reaction of the phosphate group with imidazole in the presence of a diimide and displacement of the imidazole leaving group with cystamine in one reaction step; and reduction of the disulfide bond of the cystamine linker with DTT. A similar procedure was described by Chu et al., Supra. The 5'-phosphorylated starting oligonucleotides are prepared as described by Maniatis et al., Supra. p. 122. Details of the synthesis of their thiol-derivatives are set forth in Example 1c. The overall phosphate-to-thiol transformation obtained by this process was estimated to be 60-75% by polyacrylamide gel analysis of [$^{32}$P]-labeled products, and susceptibility of clearance of 5'-$^{32}$PO$_4$ label of unreacted phosphorylated oligonucleotide by alkaline phosphatase treatment, as described in Example 1d.

The thiol-derivatized oligonucleotides are coupled with the bromoacetyl-derivatized polyacrylamide solid supports under an atmosphere of nitrogen (see also Example 1e). The attachment of thiol-oligonucleotides to the supports can be monitored using radiolabeled nucleic acids. The coupling efficiency of thiol-functionalized oligonucleotides to the bromoacetyl-derivatized solid supports is dependent on the pH of the reaction, with pH of about 9.0 being preferred. We have found a considerable variability in the attachment efficiencies in these experiments, probably due to the susceptibility of the reactive thiol group to air oxidation in storage and during the course of the reaction. The overall attachment efficiencies were found to be between about 3.5% and 48%. However, since the yields of the coupling experiments are calculated as percentages of cpms of the total radioactivity introduced in the system, due to the incomplete conversion of the 5'-phosphorylated oligonucleotides to their thiol-derivatives, the actual yields are considerably higher. Moreover, following this method, more than 99% of the oligonucleotides are attached to the solid support through their 5'-termini. This is a striking advantage over other systems known in the art, for example Sephacryl TM dextran beads, where merely about 50–55% of the Oligonucleotides are end-attached.

During the course of this work, we found it beneficial to: (1) use fresh thiol oligonucleotides for the coupling reaction; (2) degas all reaction solutions prior to use; and (3) carry out the coupling under an inert atmosphere.

The hybridization potential of thiol-oligonucleotides immobilized on bromoacetyl polyacrylamide supports was evaluated using either a $^{32}$P-labeled oligonucleotide in a direct capture experiment, or a single-stranded 7Kb plasmid DNA target in a sandwich format. The oligonucleotides immobilized according to the invention generally gave better results than Sephacryl TM dextran beads for direct capture of target oligonucleotides in this construction. The results were somewhat worse in case of sandwich capture of long target DNA.

Using the reverse format, bromoacetyl-derivatized oligonucleotides are coupled with thiol-derivatized polyacrylamide solid supports. The introduction of thiol functionalities on polyacrylamide matrices can be achieved by reacting hydrazide-polyacrylamide supports with N-acetylhomocysteine thiolactone, essentially as described in Example 2a hereinafter. The extent of derivatization can be determined, by titration of the thiol group with Ellman's reagent, as hereinbefore described. The conversion usually is between about 4% and about 15%, and is strongly dependent on the amount of hydrazide groups in the solid supports; supports with higher hydrazide substitution levels being preferred. Since the conversion of hydrazide groups into thiol groups is low, there are always unreacted hydrazide groups left that are available for further derivatization. Matrices with mixed functionalities, in which the residual hydrazide groups are converted, for example, into carboxyl or trinitrophenyl groups, without modifying the thiol-functionalities, are easy to prepare by literature-known processes and may have advantages in certain hybridization reactions, by reducing non-specific absorption of the negatively charged nucleic acids, due to the anionic properties of carboxyl and trinitrophenyl groups. Treatment of the polyacrylamide supports with glutaric anhydride and/or iodoacetic acid converts the hydrazide and sulfhydryl functionalities to carboxylic groups. These supports were found to provide better non-specific adsorption results and are, therefore, preferred for use in direct capture experiments.

Oligonucleotides derivatized at their 5'-termini with bromoacetyl groups can, for example, be prepared by reacting 5'-aminohexyl-phosphoramidate oligonucleotides with bromoacetic acid-N-hydroxysuccinimide ester. The performance of the reaction is further illustrated in the examples. The phosphate-to-bromoacetamide transformation is about 60–70% determined by polyacrylamide gel analysis of the [$^{32}$P]-labeled products, and susceptibility of cleavage of 5'-$^{32}$PO$_4$ label of unreacted phosphorylated oligonucleotides to alkaline phosphatase treatment.

The covalent attachment of the bromoacetyl-oligonucleotides to thiol-derivatized polyacrylamide solid supports is illustrated in the examples. The coupling efficiencies are between about 3% and about 30%, depending on the pore size (molecular weight exclusion limit) of the solid support employed. As noted earlier, the actual coupling efficiencies are higher, since these figures do not reflect the incomplete conversion of the 5'-phosphorylated oligonucleotides to their bromoacetyl derivatives. Surprisingly, more porous matrices with high exclusion limits provide substantially better coupling results than the highly cross-linked variants.

The hybridization potential of bromoacetyl oligonucleotides immobilized on thiol-derivatized solid supports was tested by direct capture of oligonucleotide targets and in sandwich format, using TAS RNA transcripts. The results were similar to those obtained with the reverse format. While the oligonucleotides immobilized on thiol-polyacrylamide supports were clearly better in direct capture of oligonucleotides than Sephacryl TM dextran beads, their capture potential was less expressed in sandwich capture experiments, especially when long targets were to be identified.

The direct capture and background properties of bromoacetyl ester derivatized oligonucleotides immobilized on thiol-polyacrylamide solid supports were also tested with oligonucleotide-alkaline phosphatase conjugates. Although the background from non-specific binding was found to be low, the greater capture potential of polyacrylamide supports was lost in the case of oligonucleotide-enzyme conjugates.

According to a particularly preferred embodiment of the invention, polyacrylamide supports with exclusion limits of about $2 \times 10^7$ daltons are employed. A typical support from this group is Trisacryl TM polyacrylamide GF-2000 (IBF Biotechnics, USA). Since, as hereinabove described, the amide hydrogens of this polyacrylamide resin are substituted with 2-hydroxymethyl-1,3-propane diol groups, before further derivatization, reactive amine groups need to be introduced, for example by transamidation with ethylene diamine. This reaction is carried out at slightly elevated temperatures, preferably at about 90° C. Thiol-derivatives of these supports are prepared in an analogous manner to the preparation of the thiol-derivatized Bio-Gel ™ polyacrylamide products. To reduce electrostatic interactions between the positively charged amine groups and the negatively charged oligonucleotide backbone, the residual unreacted amine groups on the Trisacryl ™ polyacrylamide supports are preferably acylated either with glutaric anhydride or succinic anhydride. The substitution level of the sulfhydryl groups on the Trisacryl ™ polyacrylamide-SH supports, determined by titration of the sulfhydryl functionalities with DTNB, is in the range of about 10 to about 16 μmoles/gr. With these supports, the coupling efficiencies to bromoacetylated oligonucleotides is about 20%, and the level of end-attachment is extremely high (about 97%). The oligonucleotide substitution level of these supports is about 60 pmoles oligonucleotide/gram support.

In hybridization studies involving direct capture of radioactively labeled oligonucleotides, Trisacryl ™ polyacrylamide-SH supports containing immobilized oligonucleotides, especially supports in which the unreacted sulfhydryl groups were alkylated with iodoacetate, performed particularly well. The oligonucleotides immobilized on Trisacryl ™ polyacrylamide-SH supports showed excellent hybridization potential also in sandwich hybridization experiments, essentially carried out as hereinabove described. The signal-to-noise ratio was about 4-times higher in sandwich hybridization experiments performed with Trisacryl ™ polyacrylamide supports than on Sephacryl ™ dextran beads.

The bromoacetylated oligonucleotides couple to thiol-derivatized polyacrylamide supports with reasonable yields, and the reproducibility of the reaction is very good. In case of the reverse format, using thiol-oligonucleotides and bromoacetyl derivatized supports, the coupling efficiencies show greater variability, probably due to the higher susceptibility of thiol-oligonucleotides to oxidation. However, both approaches provide extremely good end-attachment results. Essentially all of the oligonucleotides (95% or more) are attached to the solid supports by their 5'-termini, by using either coupling methodology of the present invention.

The hybridization potential of oligonucleotides immobilized on polyacrylamide solid supports following any of the processes disclosed in the present invention, is very good in direct capture experiments, primarily due to the superior direct-capture ability of end-attached oligonucleotides. In sandwich hybridizations with TAS RNA products or long, single-stranded DNA fragments, the polyacrylamide supports having large pore sizes perform especially well in contrast to their highly cross-linked counterparts. The results can be further improved by functionalization of these porous supports, e.g., with carboxyl groups. The best results were clearly obtained with polyacrylamide supports having an exclusion limit of about $2 \times 10^7$ daltons (Trisacryl ™ polyacrylamide GF 2000).

EXAMPLES

Reference Example 1

Test methods a. Direct capture of $^{32}$P-labeled targets on oligonucleotide-derivatized supports The bead samples (50 mg) were aliquoted into 1 ml eppendorf tubes, and the supernatant was removed after centrifugation. Prehybridization in 250 μl of 5× SSPE [0.75M NaCl, 50 mM NaH$_2$PO$_4$, pH 7.4, and 5 mM ethylene diamine tetracetate.4 Na (EDTA)], 10% dextran sulfate, 0.1% sodium dodecyl sulfate (SDS) was carried out at 37° C. for 30 minutes, after which the supernatant was drawn off. Samples of complementary and non-complementary $^{32}$P-labeled oligonucleotides (approximately 30 bases) were preincubated at 65° C. for 5 minutes and then added to the bead samples (typically 3.75 fmoles oligonucleotide/100 μl hybridization buffer). The beads were incubated at 37° C. for 1 hour with occasional shaking. After washing with 5×1 ml of 2× SSC (0.3M NaCl, 0.03M Na citrate, pH 7.0) at 37° C., the amount of label bound to the supports was determined by Cerenkov counting.

b. Sandwich hybridization of TAS-generated RNA transcripts on solid supports

Samples of Bio-Gel ™ polyacrylamide (Bio-Rad, USA) or Trisacryl ™ polyacrylamide (IBF Biotechnics, USA) (50 mg) were prehybridized as outlined above.

The target, DNA or RNA, was denatured at 65° C. for 5 minutes immediately prior to hybridization. Solution hybridization of the target RNA (0.5 fmoles) with a complementary, $^{32}$P-labeled detection oligonucleotide (5 fmoles) was performed in a total volume of 20 μl in 5× SSPE, 10% dextran sulfate, 0.1% SDS for 2 hours at 42° C. The sample was then diluted to 100 μl with hybridization buffer and added to the solid support. Sandwich hybridization was performed at 37° C. for 1 hour with occasional shaking. Finally, the beads were washed with 5×1 ml 2× SSC at 37° C. Non-complementary RNA target was used as a control to determine the level of non-specific binding in the assay.

c. Direct capture of alkaline phosphatase-oligonucleotide conjugates on solid supports Oligonucleotide-containing Bio-Gel ™ polyacrylamide or Trisacryl ™ polyacrylamide supports (50 mg) were prehybridized with 250 μl of 5× SSC, 10% dextran sulfate, 0.1% SDS, 1% bovine serum albumin fraction V bovine serum albumin fraction V (BSA) in 1 ml eppendorf tubes for 30 minutes at 37° C. Complementary and non-complementary oligonucleotide-alkaline phosphatase conjugates were diluted with 0.1M Tris, 0.1M NaCl, 1% BSA, pH 7.5, and preincubated at 55° C. for 5 minutes. After addition of the conjugate (37.5 fmoles) in 100 μl of hybridization buffer, the 30 mixture of conjugate and Sephacryl beads was incubated at 42° C. for 1 hour with occasional shaking. The supports were washed with 4×1 ml of 2× SSC at 37° C. The bead samples and washes were treated with 1 ml 0.1 mM p-nitrophenyl phosphate in 0.1M Tris, 0.1M NaCl, 0.01M MgCl$_2$, pH 9.5. After development of color at room temperature for 1 hour, the formation of p-nitrophenolate was measured by reading the absorbance at 410 nm.

d. TNBS test for hydrazides and amines

Filtrates for hydrazide or amine-derivatized supports were tested for free hydrazide or ethylenediamine as follows. Two ml of filtrate were treated with 1 ml of saturated Na$_2$B$_4$O$_7$ and 3 drops of 3% aqueous trinitrobenzene sulfonate (TNBS), with thorough mixing. The appearance of a purple or orange color after one minute indicated the presence of hydrazine or amine, respectively.

e. DTNB test for sulfhydryl and bromoacetyl substitution determination

A sample of derivatized support (1–20 mg wet weight) was reduced with 500 μl of 20 mM dithiothreitol (DTT) in 0.05M $K_2HPO_4$, 1 mM EDTA, pH 8.0, for 30 minutes in a 1-ml eppendorf tube and washed with 3×1 ml of 0.05M $K_2HPO_4$, pH 8.0, after the supernatant had been removed. The beads were then treated with 1 ml of 1 mM 5,5'-dithiobis(2-nitrobenzoic acid) (DTNB) in 0.05M $K_2HPO_4$, pH 8.0. The absorbance of the supernatant was monitored at 412 nm after 15 minutes ($\epsilon$=13,600 for released thiophenolate).

Reference Example 2

Preparation of hydrazide derivatives of Bio-Gel TM polyacrylamide beads

Hydrazide derivatives of Bio-Gel TM polyacrylamide beads (Bio-Rad, USA) were prepared using the procedure of Inman (Meth. Enzymol. 34(B):30, 1974). Typically, a 20 ml solution of 6M hydrazine at 50° C. was added to 1 gram of dry resin. After 40 minutes, the excess reagent was removed by washing the beads with 0.2M NaCl until the filtrate gave a negative test with 2,4,6-trinitrobenzene sulfonic acid (TNBS). The derivatized beads were sucked dry for 15 minutes, weighed, and suspended in 10 mM Tris, 1 mM EDTA (TE), pH 8.0, or 0.1M $K_2HPO_4$, pH 8.0.

The non-specific binding of [$^{32}$P]-labeled oligonucleotides, alkaline phosphatase-oligonucleotide conjugates, alkaline phosphatase with BSA, and linker-derivatized alkaline phosphatase with BSA was determined with the above supports, and the results presented in Table I.

TABLE I

NON-SPECIFIC BINDING ON BIO-GEL TM POLYACRYLAMIDE
P-60 HYDRAZIDE BEADS

| Bio-Gel TM polyacrylamide Hydrazide | % Bound to Beads | | | | |
|---|---|---|---|---|---|
| | [$^{32}$P] Oligo | Conjugate | Conjugate + BSA | Alkaline Phosphatase with BSA | Alkaline Phosphatase-Linker w/BSA |
| 31 micromole/gm | 0.26 | 11.3 | 5.2 | 1.95 | 5.90 |
| 62 micromole/gm | 0.23 | 9.8 | — | — | — |
| 125 micromole/gm | 0.32 | 13.7 | 4.1 | — | — |
| 500 micromole/gm | 0.41 | 13.5 | 8.6 | 1.2 | 4.49 |

The non-specific binding of [$^{32}$P]-labeled oligonucleotides was low and was not dependent on the level of substitution of the hydrazide residues on Bio-Gel TM polyacrylamide. However, backgrounds from enzyme-oligonucleotide conjugates were much higher (9.8–13.7%) when no BSA was used in the hybridization solutions. This indicated that the enzyme component of the conjugate was largely responsible for this interaction. The addition of BSA to the hybridization mixture was found to be partially effective in eliminating non-specific binding of the enzyme-oligonucleotide conjugate. Parallel experiments using alkaline phosphatase and alkaline phosphatase-linker show that derivatization of the enzyme with the linker was primarily responsible for the non-specific binding.

Example 1

Covalent attachment of thiol-oligonucleotides to bromoacetyl Bio-Gel TM polyacrylamide beads a. Acylation of Bio-Gel TM polyacrylamide hydrazide beads with N-succinimidyl bromoacetate Synthesis of N-succinimidyl bromoacetate:

Bromoacetic acid (20 mmoles) was treated with dicyclohexyl-carbodiimide (22 mmoles, 1.1 equivalents) and N-hydroxysuccinimide (22 mmoles) in 30 ml $CH_2Cl_2$ at 4° C. according to the procedure of M. S. Bernatowicz and G. R. Matsueda (Anal. Biochem. 155:95, 1986) to give the N-succinimidyl bromoacetate as a white solid.

Acylation:

A 1 gram (wet weight) sample of Bio-Gel TM polyacrylamide hydrazide beads (50 μmoles/dry gram) was washed with 2×50 ml 0.1M $K_2HPO_4$, pH 7.0, and resuspended in 5 ml of this buffer. The suspension was cooled to 0° C. in an ice bath, and N-succinimidyl bromoacetate (10 mole equivalents relative to hydrazide groups) in 250 μl N,N-dimethylformamide (DMF) was added dropwise with stirring. The reaction mixture was allowed to come to room temperature over 30 minutes. After cooling to 0° C. again, another aliquot of N-succinimidyl bromoacetate was added and the reaction mixture was stirred for 30 minutes at room temperature. The beads were filtered through a sintered glass funnel (porosity C) and washed with 50 ml 0.1M $K_2HPO_4$, pH 7.0. The acylated beads were stored in 0.1M $K_2HPO_4$ at 4° C.

To determine the level of substitution, the supports were exposed to a large excess of DTT to effect a quantitative bromoacetyl-to-thiol functionality conversion.

The thiol groups were then titrated with Ellman's reagent [5,5-dithiobis-(2-nitrobenzoic acid)] (see Reference Example 1e). From Table II it can be seen that the conversion of hydrazide groups to bromoacetyl functionalities proceeded with an efficiency of 56%, 43%, and 40% for P-10, P-60, and P-200, respectively, while the reaction with the P-2 support was less efficient.

TABLE II

REACTION OF HYDRAZIDE
WITH BROMOACETIC ACID
NHS ESTER POLYACRYLAMIDE SUPPORTS

| Support Type | μ moles $NHNH_2$/g | Molar excess NHSBrAc | μ moles $CH_2Br$/g | % $NHNH_2$ converted |
|---|---|---|---|---|
| P-2-$CH_2Br$ (MW cut-off 2,000) | 50 | 20 | 8.0 | 16.0 |
| P-10-$CH_2Br$ (MW cut-off 10,000) | 50 | 20 | 27.9 | 55.8 |

TABLE II-continued

REACTION OF HYDRAZIDE WITH BROMOACETIC ACID NHS ESTER POLYACRYLAMIDE SUPPORTS

| Support Type | μ moles NHNH$_2$/g | Molar excess NHSBrAc | μ moles CH$_2$Br/g | % NHNH$_2$ converted |
|---|---|---|---|---|
| P-60-CH$_2$Br (MW cut-off 60,000) | 50 | 20 | 21.6 | 43.2 |
| P-200-CH$_2$Br (MW cut-off 200,000) | 50 | 20 | 20.3 | 40.5 |

Non-specific binding experiments with oligonucleotide-alkaline phosphatase conjugates (see Reference Example 1c) were carried out with three types of P-2 and P-60 supports (Table III).

TABLE III

NON-SPECIFIC BINDING WITH 50 F MOLES CONJUGATE (% BOUND)

| Type of Support | —NHNH$_2$ | —CH$_2$Br —NHNH$_2$ | —CH$_2$Br —COOH |
|---|---|---|---|
| P-2 | 1.57 | 1.01 | 0.71 |
| P-60 | 7.3 | 3.5 | 1.4 |

A decrease in non-specific adsorption was observed for both supports when the hydrazide functionality was capped with bromoacetyl groups. Since the reaction of hydrazide supports with bromoacetic acid N-hydroxysuccinimide ester does not result in a quantitative conversion (see Table II, last column), the residual hydrazide groups are still available for derivatization.

b. Glutarylation of bromoacetyl Bio-Gel ™ polyacrylamide beads

A 1.0 gram (wet weight) sample of bromoacetyl Bio-Gel ™ polyacrylamide beads (50 μM hydrazide/dry gram) was washed with 0.1M NaCl and suspended in 20 ml of this solution in a glass beaker. To the stirred suspension was added 100 mg of glutaric anhydride. The pH of the suspension was maintained at 4.0–4.2 with 3M NaOH, while the reaction mixture was stirred for 15 minutes. Then, another 100 mg of anhydride was added, and the reaction mixture was stirred for a further 15 minutes. The beads were then washed with 3×40 ml 0.1M K$_2$HPO$_4$, pH 7.0, by allowing the beads to settle in a conical tube and decanting the supernatant.

Figure 2:
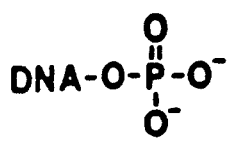
FIG. 2 shows the synthetic route of thiol-oligonucleotides and their coupling to bromoacetyl-derivatized Bio-Gel TM polyacrylamide supports. (The residual hydrazide groups are converted to carboxyl groups to lower non-specific binding.)
Figure 2:
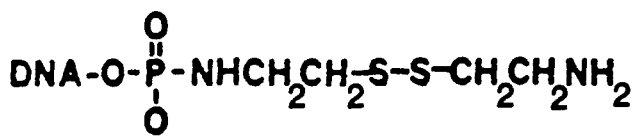
Figure 2:
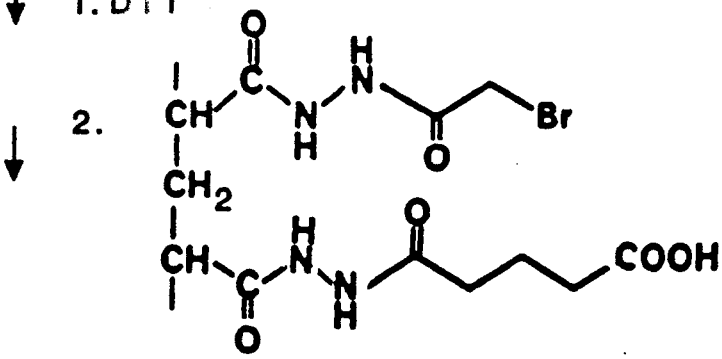
Figure 2:
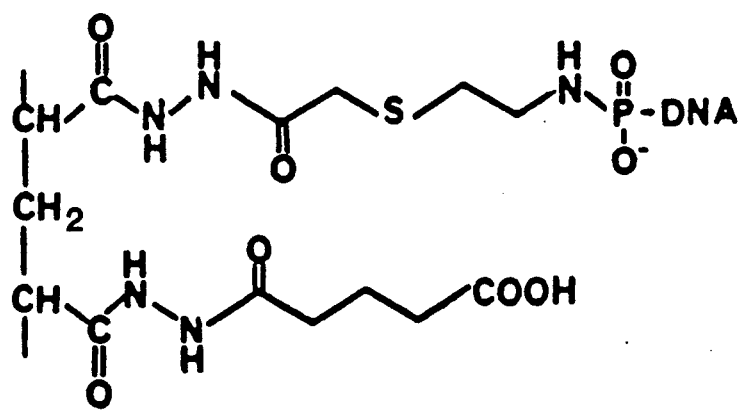

When the bromoacetyl supports were treated with excess glutaric anhydride, as described above, a hydrazide-to-carboxyl transformation was obtained. The carboxyl group in these bifunctional supports provided an additional reduction in non-specific binding of the enzyme-oligonucleotide conjugates (Table III, column 3).

c. One-step preparation of 5'-cystaminyl phosphoramidate derivatives of oligonucleotides The 5'-phosphorylated oligonucleotide [Maniatis et al., Supra] in a silanized eppendorf tube was treated with 300 μl of a 0.1M imidazole, 0.15M 1-ethyl-3-(3-dimethylaminopropyl)-carbodiimide.HCl (EDC), 0.25M cystamine dihydrochloride, pH 6.0, and let stand at room temperature overnight. The modified oligonucleotides were precipitated with ethanol/LiCl, washed with 300 μl H$_2$O, and precipitated again. Yields of 86% were obtained using this procedure. The reaction is illustrated in FIG. 2.

d. Determination of level of cystamine attachment to 5'-phosphorylated oligonucleotides A 50-pmole sample of $^{32}$P-labeled cystaminyl-derivatized oligonucleotide was treated with 1 μl stock calf intestine alkaline phosphatase (Boehringer Mannheim, EIA grade) and the volume made up to 100 μl with 0.1M Tris, 0.1M NaCl, 0.01M MgCl$_2$, pH 9.5. The reaction was allowed to proceed for 2 hours. The sample was then applied on a 5 ml column of Sephadex G-50 and eluted with TE, pH 8.0. The first and second radioactive peaks were collected, corresponding to cystaminyl-derivatized oligonucleotides and free inorganic phosphate (cleaved from 5'-phosphorylated oligonucleotide), respectively. The peaks were counted by Cerenkov counting to estimate the yield of cystamine attachment.

e. Covalent attachment of 5'-cystaminyl-derivatized oligonucleotides to bromoacetyl-Bio-Gel ™ polyacrylamide beads The cystaminyl-containing oligonucleotide was reduced with 300 μl 0.1M DTT, 0.2M HEPES, 0.001M EDTA, pH 7.7, for 1 hour at room temperature. The product was precipitated with EtOH/LiCl and washed twice with 0.2M HEPES, 0.001M EDTA. Typically, 50 mg of beads were treated with 25 pmoles of reduced oligonucleotide in 150 μl 0.1M K$_2$HPO$_4$, pH 9.0, and agitated under N$_2$ on a rotary mixer overnight. As a control to determine non-specific binding, a 5'-phosphorylated oligonucleotide was added to a sample of beads under the same conditions. The beads were washed with: (a) 3×1 ml 0.1M Na$_2$P$_2$O$_7$, pH 7.5, and (b) 3×1 ml 0.015M NaOH, pH 12. $^{32}$P-labeled oligonucleotides were used as controls to estimate end-attachment efficiencies.

The attachment of the thiol-derivatized oligonucleotides to the bromoacetyl-Bio-Gel ™ polyacrylamide supports was monitored using radiolabeled nucleic acids, and the results are summarized in Table IV.

TABLE IV

COUPLING YIELDS[1] OF BROMOACETYL SUPPORTS WITH THIOL-OLIGONUCLEOTIDES

| | Type of Support | | % 86-31-SH bound | % 86-31-PO$_4$ bound | % end-attachment | %[2] 87-416-SH bound | % 87-416-PO$_4$ bound | % end-attachment |
|---|---|---|---|---|---|---|---|---|
| 1 | P-2-CH$_2$Br | | 3.46 | 0.08 | 98 | | | |
| 2 | P-10-CH$_2$Br | | 9.51 | 0.44 | 95 | | | |
| 3 | P-60-CH$_2$Br | | 15.82 | 0.28 | 98 | | | |
| 4 | P-60-CH$_2$Br | | 36.7 | 0.84 | 98 | | | |
| 5 | P-60-CH$_2$Br | | 48.4 | 0.15 | 100 | | | |
| 6 | P-200-CH$_2$Br | | 17.00 | 0.35 | 98 | | | |
| 7 | P-60-CH$_2$Br | | | | | 16.1 | 0.7 | 96 |
| 8 | P-60-CH$_2$Br | —CO$_2$H | | | | 11.9 | 0.3 | 98 |

[1]Reactions were done in potassium phosphate pH 9.00, for 16 hours, and non-specifically bound oligonucleotides were removed by 3 washes with sodium pyrophosphate, followed by 3 washes with NaOH, pH 12.00.
[2]End attached (%) = [(oligo-SH) − (oligo-PO$_4$)] ÷ oligo-SH Since the yields of the coupling experiments are percentages of cpms of the total radioactivity introduced in the reaction, the actual yields are in fact higher, due to the incomplete conversion of 5'-phosphorylated oligonucleotides to their thiolated derivatives. It can readily be seen that essentially all of the oligonucleotides are end-attached via thioether bonds following this coupling strategy. The variability in the attachment efficiencies (see entries 3-6, Table IV), was ascribed to the susceptibility of the reactive thiol group to air oxidation in storage or during the course of the reaction. While the overall attachment efficiencies of oligonucleotide to polyacrylamide supports (3-48%) were lower than to Sephacryl ™ dextran (70%), this coupling strategy provides a superior method for obtaining end-attached oligonucleotides.

The hybridization potential of oligonucleotides immobilized on P-60 supports (MW 60,000 cut-off) was evaluated using [$^{32}$P]-oligonucleotide-length target and a 7 kb DNA single-stranded plasmid in a sandwich format. The P-60 support was chosen for the study, since this matrix displayed the best attachment efficiencies in the coupling reaction with thiol-oligonucleotide derivatives. The results of the capture experiments are summarized in Table V.

the rate of duplex formation. At this stage, it was reasoned that it would be beneficial to reverse the functionalities in the coupling reaction. An impediment to obtaining better coupling efficiencies, and hence higher substitution levels, was the susceptibility of the thiol-oligonucleotide derivative to oxidation. The following Examples 2 and 3 discuss our results with the reverse format.

Example 2

Covalent attachment of bromoacetyl-oligonucleotides to Bio-Gel ™ polyacrylamide-SH a. Preparation of sulfhydryl derivatives of Bio-Gel ™ polyacrylamide supports One gram (wet weight) of Bio-Gel ™ polyacrylamide hydrazide beads (500 μmoles-NHNH$_2$/dry gram) was equilibrated with 0.5M NaHCO$_3$, pH 9.7. To a suspension in 5 ml were added 30 mole equivalents (relative to NHNH$_2$ groups) of N-acetylhomocysteine thiolactone, and the mixture was shaken at room temperature overnight. The beads were washed with 300 ml 0.1M NaCl and stored in TE, pH 8.0, or 0.1M

TABLE V

HYBRIDIZATION EXPERIMENTS WITH BROMOACETYL-DERIVATIZED POLYACRYLAMIDE SUPPORTS

| 86-31 immobilized support | Oligonucleotide Target | | | Sandwich with with 7 kb Target | | | |
|---|---|---|---|---|---|---|---|
| | f moles target | 86-32 (complementary) | 86-31 (non-complementary) | f moles target | PHIV-1 (complementary) | PHIV-2 (complementary) |
| —CH$_2$Br P-60- —NHNH$_2$ | 0.5 | 89 | 0.2 | 0.5 | 8.3 | 0.85 |
| —CH$_2$Br P-60- —COOH | 0.5 | 74 | 0.15 | | | |
| Sephacryl beads | 0.5 | 54 | 0.15 | 0.5 | 25 | 0.4 |

As seen in the Table, both types of P-60 oligonucleotide supports proved to be better than Sephacryl ™ dextran beads for direct capture of oligonucleotides. The support-bearing carboxyl functionalities on the surface displayed a non-specific binding identical to the Sephacryl ™ dextran control and were marginally better than the P-60 hydrazide matrix. The polyacrylamide-based support showed a poorer ability than Sepha- K$_2$HPO$_4$, pH 8.0. The reaction is illustrated in FIG. 1, reaction B. The level of sulfhydryl substitution was determined by titrating with 5,5'-dithiobis(2-nitrobenzoic acid) (DTNB) and monitoring the release of 3-carboxylato-4-nitrothiophenolate at 412 nm. The conversion was found to be dependent on the substitution level of hydrazide groups in the solid support, as illustrated in Table VI.

TABLE VI

REACTION OF HYDRAZIDE SUPPORTS WITH N-ACETYLHOMOCYSTEINE LACTONE

| | Type of support | | μ mole NHNH$_2$/gm | molar excess thiol lactone | % NHNH$_2$ conversion | μ mole SH/gm |
|---|---|---|---|---|---|---|
| 1 | P-2-SH | | 50 | 100 | 3.8 | 1.9 |
| 2 | P-2-SH | | 500 | 30 | 9.9 | 49.4 |
| 3 | P-10-SH | | 50 | 100 | 7.1 | 3.6 |
| 4 | P-60-SH | | 50 | 100 | 7.6 | 3.6 |
| 5 | P-200-SH | | 50 | 100 | 4.3 | 2.2 |
| 6 | P-200-SH | —SH[1] | 500 | 30 | 14.2 | 70.3 |
| 7 | P-200 | —CO$_2$H | 500 | 30 | 15.3 | 76.3 |
| 8 | P-300-SH | —SH[2] | 500 | 20 | 10.4 | 52.2 |
| 9 | P-300 | -TNPH —SH[3] | 500 | 20 | 10.0 | 50.2 |
| 10 | P-300 | —CO$_2$H | 500 | 20 | 9.2 | 45.9 |

1. Conversion of hydrazide groups in P-200-SH support with glutaric anhydride.
2. Conversion of hydrazide groups in P-300-SH support with trinitrophenyl sulfonate.
3. Conversion of hydrazide groups in P-300-SH supports with glutaric anhydride.

cryl ™ dextran beads to detect long target DNA in sandwich hybridizations and also displayed higher backgrounds. This result suggested that perhaps a substantial portion of the immobilized oligonucleotides was in the interior of the support, and therefore was not accessible to the long target fragment for hybridization. Consequently, only a small portion of the immobilized oligonucleotide would be available on the surface for b. Glutarylation of sulfhydryl-Bio-Gel ™ polyacrylamide beads A one-gram sample of sulfhydryl Bio-Gel ™ polyacrylamide was suspended in 20 ml 0.1M NaCl, and two 100-mg aliquots of glutaric anhydride were added at 15-minute intervals. The pH was maintained near 4.0 with 3M NaOH. After a total reaction time of 30 minutes, the beads were washed with 0.1M NaCl. Hydrolysis of thioesters was then carried out with 10 ml 0.1M Tris.HCl, pH 8.5, for 1 hour at room temperature.

Further conversion of the remaining hydrazide groups in the thiol supports with glutaric anhydride or trinitrobenzene sulfonate provided matrices with mixed functionalities ($\approx$SH and $\approx$COOH, or $\approx$SH and $\approx$TNPH, respectively). No modification of the thiol groups was observed in these reactions (Table VI, compare 6 and 7, and 8-10). The rationale behind the syntheses of these mixed supports was to exploit the anionic or dipolar properties of the carboxyl or TNPH groups in reducing non-specific adsorption of negatively charged nucleic acids in hybridization reactions. A family of thiol-functionalized polyacrylamide supports, spanning a wide range of exclusion volumes, was thus prepared, having thiol substitution levels varying from 2-76 $\mu$moles per gram of material.

c. Preparation of bromoacetyl derivatives of oligonucleotides

Figure 3:
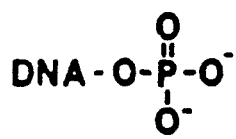
FIG. 3 is a reaction chart of the synthesis of bromoacetyl oligonucleotides.
Figure 3:
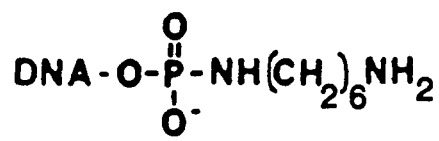
Figure 3:
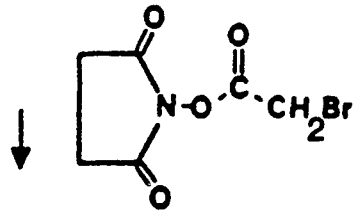
Figure 3:
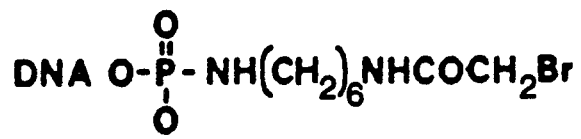

A 5'-phosphorylated oligonucleotide in a silanized eppendorf tube was treated with 300 $\mu$l of 0.25M hexanediamine HCl, 0.1M methylimidazole, 0.15M EDC, pH 6.0, at room temperature for 20 hours. The amine derivative was precipitated twice with EtOH/LiCl and redissolved in 285 $\mu$l of 0.2M HEPES, pH 7.7. A 15-$\mu$l aliquot of a 10-mg/ml solution of N-succinimidyl bromoacetate in DMF was added. After a reaction time of 1 hour, the oligonucleotide was precipitated twice with EtOH/LiCl. The reaction is illustrated in FIG. 3. The overall phosphate-to-bromoacetamide transformation was estimated to be 60-70% by polyacrylamide gel analysis of [$^{32}$P]-labelled products, and susceptibility to cleavage of the 5'$^{32}$PO$_4$ group (unreacted phosphorylated oligonucleotide) by alkaline phosphatase treatment.

d. Covalent attachment of 5'-bromoacetyl-derivatized oligonucleotides to sulfhydryl-Bio-Gel TM polyacrylamide beads Sulfhydryl-Bio-Gel TM polyacrylamide support (1 gram wet weight) was reduced with 5 ml 20 mM DTT in 0.05M K$_2$HPO$_4$, pH 8.0, for 1 hour, then washed with 2×40 ml 0.05M K$_2$HPO$_4$, pH 8.0, followed by 2×40 ml 0.1M triethylammonium phosphate, 1 mM EDTA, pH 9.0. Five hundred pmoles of bromoacetyl-derivatized oligonucleotide was dissolved in 1 ml TEAP, EDTA, pH 9.0, and added to the resin in a 5-ml polypropylene tube. After purging the tube with N$_2$ and sealing with parafilm, the bead sample was agitated on a rotary mixer overnight. The beads were washed with: (a) 3×10 ml 0.1M Na$_2$P$_2$O$_7$, pH 7.5, and (b) 2×10 ml TE, pH 8.0. Unreacted sulfhydryl groups were capped by reducing the support with 3 ml 20 mM DTT in 0.05M K$_2$HPO$_4$, pH 8.0, for 30 minutes. After removal of excess DTT and equilibration in 0.1M TEAP, 1 mM EDTA, pH 9.0, 3 ml of 5 mM iodoacetic acid in the same buffer was added and allowed to react for 1 hour. After filtration of unreacted reagent through a sintered glass funnel (porosity C), the bead samples were stored in TE, pH 8.0, at 4° C.

Figure 4:
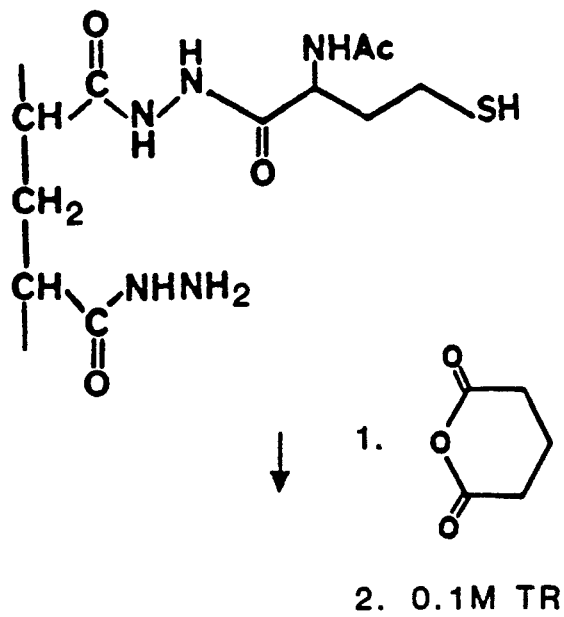
FIG. 4 shows the acylation of thiol-derivatized Bio-Gel TM polyacrylamide supports and the use of the polyacrylamide matrices with mixed functionalities in coupling with bromoacetyl oligonucleotides.
Figure 4:
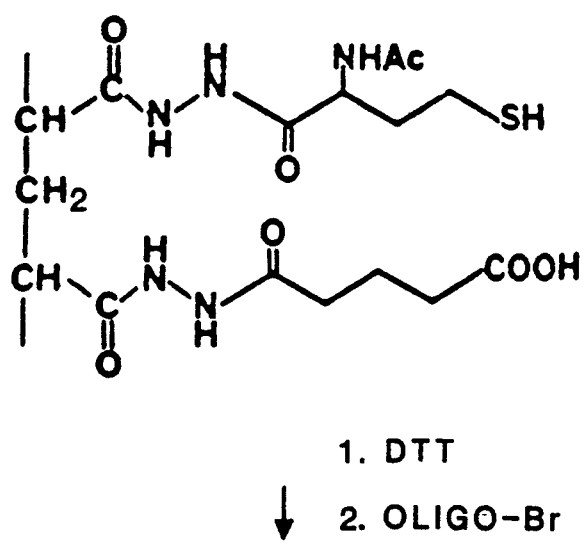
Figure 4:
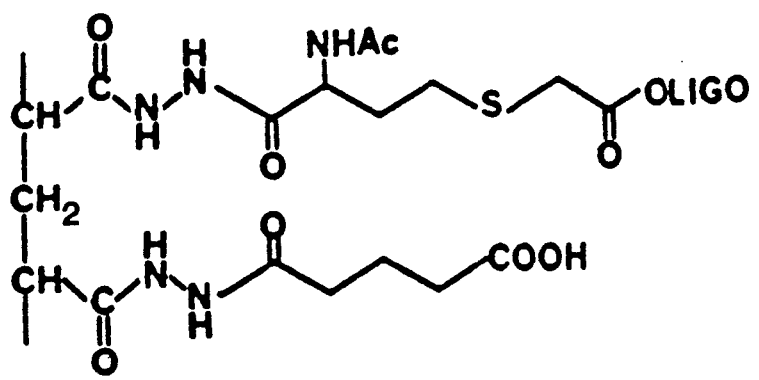

Coupling Efficiencies of Bromoacetyl Oligonucleotides to Thiol Polyacrylamide Supports The immobilization studies concentrated on P-2, P-200, and P-300 matrices, because of their vastly different exclusion volumes. It was hypothesized that the highly cross-linked P-2 support (MW cut-off 2,000) would have all the oligonucleotides attached on the surface, and hence be available for capture. The small pore size would also prevent the inclusion of nucleic acids during the hybridization and thereby be beneficial in reducing non-specific binding. In contrast, the P-200 and P-300 supports (MW cut-off 200,00 and 300,000) are closer to Sephacryl TM dextran (MW cut-off 20,000,000) in structural features in having large pores in the matrix. The results of the coupling reaction (see FIG. 4) of these derivatives with these thiol-polyacrylamide supports are shown in Table VII.

TABLE VII

COUPLING YIELDS OF THIOL SUPPORTS WITH BROMOACETYL OLIGONUCLEOTIDES

| | Support (500 $\mu$ mole NHNH$_2$ initial substitution time) | | 86-31-CH$_2$Br % attached | 86-31-PO$_4$ % attached | % end attchmt |
|---|---|---|---|---|---|
| 1 | P-2-SH | | 3.5 | 0.2 | 94 |
| 2 | P-200-SH | —SH | 28.6 | 0.5 | 98 |
| 3 | P-200 | -TNPH | 29.3 | 0.5 | 98 |
| 4 | P-300-SH | —SH | 29.9 | 1.7 | 94 |
| 5 | P-300 | —CO$_2$H | 22 | 0.5 | 98 |

The coupling with the P-2 support proceeded in low yields, even though the thiol concentration on the matrix greatly exceeded the oligonucleotide concentration in the reaction. P-200 and P-300 supports provided satisfactory yields and, in contrast to the reverse format, were consistently reproducible. As was noted earlier, the actual yields are higher than the values reported, due to the incomplete conversion of 5'-phosphorylated oligonucleotides to their bromoacetyl derivatives. The other factors to note are: (1) additional functionalization of the thiol supports with COOH or TNPH groups does not have a significant effect on the attachment efficiencies (entries 2 and 3, and 4 and 5); (2) the reaction with bromoacetyl oligonucleotides results in end-attachment of the nucleic acid to the support, as evidenced by the minimal binding of the phosphorylated oligonucleotide control; (3) a comparison of the reactivity of bromoacetyl oligonucleotides with P-200 thiol supports indicated that the displacement of bromide by the thiol groups on the support was 30% more efficient than addition to the 5' maleimide-derivatized oligonucleotide; and (4) the optimum pH for coupling was determined to be pH 9.0; higher coupling efficiencies are obtained using triethylammonium phosphate as the coupling buffer, compared to potassium phosphate.

Hybridization Characteristics of Thiol Supports

The hybridization of oligonucleotides on polyacrylamide thiol supports was tested by direct capture of oligonucleotide targets and in a sandwich format with TAS-generated RNA transcripts. Two sets of experiments are summarized in Table VIII.A., which compares P-2 and P-200 supports with Sephacryl TM dextran beads.

TABLE VIII

HYBRIDIZATION STUDIES WITH THIOL SUPPORTS

| | | Oligonucleotide (direct capture) | | | TAS (sandwich) | | | 7 kb target (sandwich) | | |
|---|---|---|---|---|---|---|---|---|---|---|
| | | Target (f moles) | 86-32 (comp) | 86-31 (non-comp) | Target (f moles) | comp | non-comp | Target (f moles) | comp | non-comp |
| A. | 86-31 Immobilized Support | | | | | | | | | |
| 1 | P-2-SH —NHNH$_2$ | 3.75 | 70.9 | 0.13 | 0.5 | 2.9 | 1.4 | | | |
| 2 | P-200-SCH$_2$—COOH —NHNH$_2$ | 3.75 | 91.9 | 0.35 | 0.5 | 8.6 | 1.9 | | | |
| 3 | Sephacryl ™ dextran beads | 3.75 | 77.7 | 0.25 | 0.5 | 12.0 | 0.85 | | | |
| B. | | | | | | | | | | |
| 1 | P-200-SH —NHNH$_2$ | 0.5 | 82 | 0.6 | | | | 0.5 | 13 | 1.9 |
| 2 | Sephacryl ™ dextran beads | 0.5 | 61 | 0.2 | | | | 0.5 | 35 | 0.3 |
| C. | | | | | | | | | | |
| 1 | P-300-SCH$_2$—CO$_2$H —NHNH$_2$ | 3.75 | 88.4 | 0.56 | 0.5 | 24 | 7 | | | |
| 2 | P-200-SH —NHNH$_2$CO$_2$H | 3.75 | 87.8 | 0.55 | 0.5 | 17 | 4 | | | |
| 3 | P-300-SCH$_2$—CO$_2$H —NHNH$_2$CO$_2$H | 3.75 | 74.5 | 0.58 | 0.5 | 15 | 2 | | | |
| 4 | Sephacryl ™ dextran beads | 3.75 | 66.5 | 0.18 | 0.5 | 13 | 0.6 | | | |

Both types of polyacrylamide supports compared very favorably with Sephacryl ™ dextran beads in showing excellent ability to capture target oligonucleotides and low non-specific binding. However, in sandwich hybridizations with TAS products, the P-2 support displayed a reduced ability to capture target, as well as a high background. Although the P-200 support was better than P-2 in sandwich hybridizations, it suffered in comparison to Sephacryl ™ dextran beads due to its 2-fold higher non-specific binding. This feature was again seen in a set of experiments comparing Sephacryl ™ dextran beads with P-200 supports in a sandwich hybridization to a 7 kb target fragment (Table VIII.B). While the polyacrylamide support was clearly superior to Sephacryl ™ dextran in oligonucleotide capture, it showed not only a lower efficiency in sandwich capture of the long target, but also an unexpected increase in non-specific binding.

To address the non-specific adsorption problem, the polyacrylamide supports (P-200 and P-300) were treated with glutaric anhydride and/or iodoacetic acid to convert the hydrazide and sulfhydryl functionalities to carboxylic groups. The hybridization results with these modified supports are shown in Table VIII.C. Consistent with our earlier observations, the direct capture of oligonucleotides by all of the polyacrylamide supports was impressive and superior to Sephacryl ™ dextran beads. While similar levels of sandwich capture of the TAS transcripts were exhibited by both the polyacrylamide and Sephacryl ™ dextran supports, the problem of non-specific adsorption surfaced again for the thiol-based supports. Capping the hydrazide and thiol groups on the support helped to reduce the background 3- to 5-fold (Table VIII.C, entries 2 and 3).

In direct capture experiments with 3.75 fmoles of target oligonucleotide, non-specific binding was observed to be ≈0.55% for all three types of polyacrylamide supports (Table VIII.C, entries 1, 2, and 3). However, in sandwich hybridizations in which 5 fmoles of detection oligonucleotide are utilized, a 5- to 14-fold increase was noted.

In order to test the premise that the long target was not captured as efficiently, and perhaps had a role to play in these increase of non-specific binding, direct capture of a labeled PCR product by polyacrylamide and Sephacryl beads was investigated. Table IX summarizes the results of the experiment.

TABLE IX

DIRECT CAPTURE OF PCR-AMPLIFIED, DOUBLE-STRANDED PRODUCT

| 86-31 immobilized support | Target (f mole) | Complementary (% capture) | Non-complementary (% capture) | Signal/ noise |
|---|---|---|---|---|
| P-300-SH | 1 | 11 | 1.1 | 10 |
| P-300-SH —CO$_2$H | 1 | 19.5 | 0.75 | 26 |
| P-200-SH —CO$_2$H | 1 | 23 | 1.7 | 13.5 |
| Sephacryl ™ dextran beads[1] | 1 | 13.5 | 0.4 | 33.8 |
| | | 17.5 | 0.65 | 26.9 |

1. Average of duplicates of two separate experiments

As seen in the Table, both carboxylated forms of the polyacrylamide supports showed better capture efficiencies of the long-stranded DNA target than Sephacryl ™ dextran beads, while the backgrounds were 2- to 3-fold higher than Sephacryl ™ dextran. These results with long target DNA closely paralleled our findings with oligonucleotide targets (Table VIII.C.). Thus, it appears that while the polyacrylamide supports can capture long targets as efficiently as (if not better than) Sephacryl ™ dextran beads, there are some other, at present unknown, factors involved in sandwich hybridizations which contribute to the increase of non-specific binding.

Hybridization of Supports With
Oligonucleotide-Enzyme Conjugates

The direct capture and background properties of the polyacrylamide support were also tested with oligonucleotide-alkaline phosphatase conjugates. The supports were incubated with complementary oligonucleotide-enzyme conjugates for 1 hour and then subjected to the standard washes to remove unbound conjugate. Color development was allowed to proceed for 1 hour using p-nitrophenyl phosphate as substrate, and the release of p-nitrophenolate was determined spectrophotometrically. A non-complementary oligonucleotide-enzyme conjugate was used as a control. Data from this study are summarized in Table X.

TABLE X
DIRECT CAPTURE OF OLIGONUCLEOTIDE-ENZYME CONJUGATES
BY POLYACRYLAMIDE SUPPORTS

| 86-31 Immobilized[1] Support | | f moles | 86-32-AP (complementary) | 86-31-AP (non-complementary) | Signal/noise (S/N) | Average S/N |
|---|---|---|---|---|---|---|
| 1 P-200-SH | $\sim CO_2H$ | 35 | .242 | .030 | 8.5 | 8.5 |
| 2 P-200-SCH$_2$CO$_2$H | $\sim CO_2H$ | 35 | .143 | .006 | 21.8 | 14.6 |
|  |  | 35 | .239 | .031 | 7.4 |  |
| 3 10% P-200-SCH$_2$CO$_2$H[2] | $\sim CO_2H$ | 35 | .135 | .002 | 61.8 | 36.47 |
|  |  | 35 | .172 | .015 | 11.0 |  |
| 4 P-300-SCH$_2$CO$_2$H | $\sim CO_2H$ | 35 | .216 | .019 | 12 |  |
|  |  | 35 | .173 | .010 | 15.8 |  |
|  |  | 35 | .222 | .025 | 8.5 | 12.1 |
| 5 10% P-300-SCH$_2$CO$_2$H | $\sim CO_2H$ | 35 | .141 | .009 | 14.3 |  |
|  |  | 35 | .190 | .026 | 7.0 | 10.7 |
| 6 Sephacryl TM dextran beads |  | 35 | .294 | .013 | 23.9 | 19.6 |
|  |  | 35 | .238 | .015 | 15.3 |  |

[1]Absorbances at 410 nm of p-nitrophenolate released from hydrolysis of p-nitrophenyl phosphate by support-bound conjugates are reported. The value reported are an average of duplicate experiments. Each row represents a different experiment performed with a duplicate set of solid supports (50 mg).
[2]Oligonucleotide-immobilized solid support was mixed with polyacrylamide support possessing carboxyl functionalities only.

The following observations can be made from the results. The average signal generated by hydrolysis of the substrate by support-bound conjugates was ≈40% higher in the case of the Sephacryl TM dextran beads when compared to polyacrylamide supports. The average of the backgrounds for both supports was nearly identical. This therefore accounted for the superior signal-to-noise ratio of Sephacryl TM dextran beads compared to the polyacrylamide supports. Keeping in mind that polyacrylamide supports are more efficient than Sephacryl TM dextran beads in the direct capture of oligonucleotides, it was therefore surprising that the capture of the conjugates proved to be contrary.

In order to determine whether the presence of the immobilized oligonucleotide on the support contributed in some manner to non-specific binding, oligonucleotide-bound support was comixed with oligonucleotide-free support in a 1:9 w/w ratio. As seen in Table X, entries 3 and 5' no significant conclusions can be made from the signal-to-noise ratios.

Example 3

Covalent attachment of bromoacetyl oligonucleotides to Trisacryl TM polyacrylamide-SH a. Preparation of amine derivative of Trisacryl TM polyacrylamide A 20-ml suspension of Trisacryl TM polyacrylamide GF-2000 (IBF, Biotechnics, USA) was pipetted into a sintered glass funnel, washed with 200 ml H$_2$O, and sucked dry for 10 minutes. The dried sample (≈11 grams) was added slowly to 20 ml of distilled ethylene diamine equilibrating at 90° C. in an oil bath. After one hour, the reaction mixture was cooled by the addition of 30 ml of crushed ice. Excess ethylene diamine was removed by washing the resin with 400 ml 0.2M NaCl, 0.001M HCl, followed by 500 ml 0.1M NaCl in a funnel. Washing was continued until the filtrate gave a negative test with TNBS reagent (Reference Example 1d).

b. Preparation of sulfhydryl derivative of Trisacryl TM polyacrylamide

Figure 5:
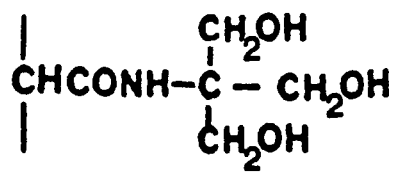
FIG. 5 is a synthetic scheme for the preparation of Trisacryl TM polyacrylamide-SH supports.
Figure 5:
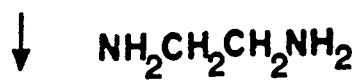
Figure 5:
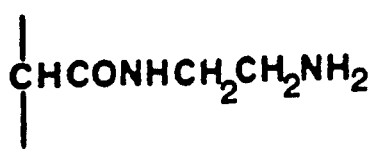
Figure 5:
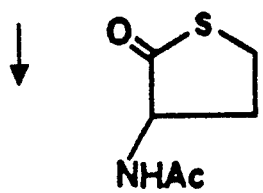
Figure 5:
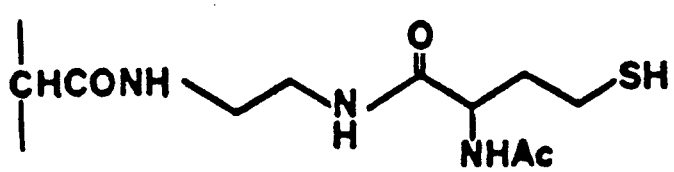
Figure 5:
Figure 5:
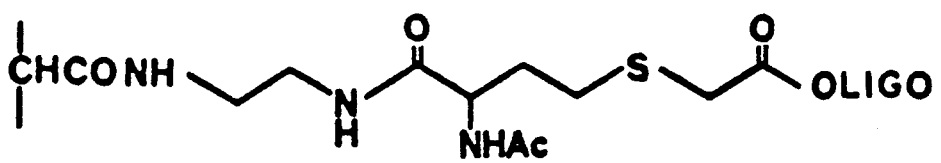

The Trisacryl TM polyacrylamide-amine support was equilibrated with 0.5M NaHCO,, pH 9.7, and the volume was adjusted to 30 ml in a 50-ml Sarstedt conical tube. Solid N-acetyl homocysteine lactone (1 gram) was added, and the tube was shaken at room temperature for 2 hours. Then, another 1 gram of reagent was added, and the sample was shaken overnight. The beads were washed with 500 ml of 0.1M NaCl, and the sulfhydryl group concentration was estimated by titrating with Ellman's reagent (DTNB) (Reference Example 1e). The reaction is illustrated in FIG. 5.

Titration of the sulfhydryl groups on the Trisacryl TM polyacrylamide-SH support indicated a substitution level of 12.3 μmoles-SH per wet gram of resin.

c. Succinylation of sulfhydryl-Trisacryl TM polyacrylamide

A 2-gram sample of Trisacryl TM polyacrylamide-SH was equilibrated in 20 ml 0.1M NaOAc, pH 6.0, and treated with 100 mg solid succinic anhydride. After shaking for 30 minutes, another 100 mg of anhydride was added to the suspension and shaken for a further 30 minutes. The beads were then equilibrated in 40 ml 0.1M Tris, pH 8.5. After 1 hour, the support was washed with TE, pH 8.0, and stored at 4° C.

d. Covalent attachment of 5 -bromoacetyl-derivatized oligonucleotides to sulfhydryl-Trisacryl TM polyacrylamide The solid support (1 gram) was reduced with DTT following the procedure used for Bio-Gel TM polyacrylamide beads (Example 2d) and equilibrated in 0.1M TEAP, 1 mM EDTA, pH 9.0. Five hundred pmoles of bromoacetyl-derivatized oligonucleotide dissolved in 1 ml TEAP/EDTA were added to the support, and the tube was purged with N$_2$ and sealed. After overnight agitation on a rotary mixer, 100 μmoles of iodoacetic acid were added and the mixture was left at room temperature for 1 hour. The beads were washed with 4×20 ml 0.1M $Na_2P_2O_7$, pH 7.5, followed by 2×20 ml TE, pH 8.0.

The reaction is illustrated in FIG. 6. The coupling reaction with [$^{32}$P]-labeled, bromoacetylated oligonucleotides resulted in 12% of the label being attached to the sulfhydryl support, and the level of end-attachment was determined to be 97%. The actual coupling yield for this reaction was estimated to be approximately 20%, based on a purity of 60–70% for the bromoacetyl oligonucleotide. Although the coupling yield was lower than those obtained with the Bio-Gel TM polyacrylamide supports (40–45%), the Trisacryl TM polyacrylamide-resin still contained a huge excess of oligonucleotide molecules relative to the amounts of target (0.5–5 fmoles) used in the hybridization experiments.

Hybridization Characteristics of Sulfhydryl-Trisacryl TM polyacrylamide Supports The initial hybridization study (Table XI.A) involving direct capture of 3.75 fmoles of [$^{32}$P]-labeled target with Trisacryl TM polyacrylamide-SH (containing oligo 86-31) showed that the non-specific binding of non-complementary target was about three times higher than for the Sephacryl TM dextran beads support (0.42% vs. 0.14%).

TABLE XI
HYBRIDIZATION STUDIES WITH TRISACRYL TM POLYACRYLAMIDE-SH

| A. Direct Capture (% Oligo Bound) | | | | |
|---|---|---|---|---|
| 86-31 Support | Target (f moles) | 86-32 (Comp.) | 86-31 (Non-Comp) | Signal/Noise |
| Trisacryl TM polyacrylamide-SH | 375 | 66.5 | 0.42 | 158.3 |
| Trisacryl TM polyacrylamide-SH ($ICH_2OOH$-treated) | 375 | 69.8 | 0.15 | 465.3 |
| Sephacryl TM dextran beads | 375 | 54.6 | 0.14 | 390.0 |

| B. TAS HIV RNA (SANDWICH) CAPTURE | | | | |
|---|---|---|---|---|
| 86-31 Support | Target (f moles) | 86-32 (Comp.) | 86-31 (Non-Comp) | Signal/Noise |
| Trisacryl TM polyacrylamide-SH ($ICH_2OOH$-treated) | 0.5 | 17.0 | 0.1 | 170.0 |
| Sephacryl TM dextran beads | 0.5 | 12.5 | 0.9 | 13.9 |

| C. Direct Capture of Oligonucleotide-enzyme Conjugates | | | | |
|---|---|---|---|---|
| 86-31 Support | Target (f moles) | 86-32-AP (Comp.) | 86-31-AP (Non-Comp) | Signal/Noise |
| Trisacryl TM polyacrylamide-SH ($ICH_2OOH$-treated) | 5 | 0.179 | 0.003 | 61.7 |
| Sephacryl TM dextran beads | 5 | 0.319 | 0.023 | 14.4 |

It was anticipated that alkylation of the unreacted sulfhydryl groups on the Trisacryl TM polyacrylamide support with iodoacetate would reduce the non-specific binding by increasing the negative charge-density of the matrix. Indeed, when the alkylated Trisacryl TM polyacrylamide support was assayed in a direct capture experiment, the non-specific binding dropped considerably to 0.15%, which was comparable to that obtained with Sephacryl TM dextran beads.

More importantly, the results from a TAS sandwich experiment (Table XI.B) using 0.5 fmoles of target RNA emphasized the superiority of Trisacryl TM polyacrylamide over Sephacryl TM dextran beads as evidenced by the higher percent capture of complementary target. Most gratifying was the extremely low non-specific background afforded by this macroporous polyacrylamide support. This was in contrast to the higher background of Bio-Gel TM polyacrylamide supports, which had been the principal cause for the lower signal/noise ratios in the TAS sandwich format.

Finally, the Trisacryl TM polyacrylamide support was tested with oligonucleotide-alkaline phosphatase conjugates to determine the level of direct capture and background properties (Table XI.C.). Incubation of complementary and non-complementary conjugates with Trisacryl TM polyacrylamide and Sephacryl TM dextran beads followed by standard washing procedures and a colorimetric assay using p-nitrophenyl phosphate was performed with 5 fmoles of conjugates. Although the capture of complementary target was higher in the case of Sephacryl TM dextran beads, the non-specific binding of the Trisacryl TM polyacrylamide was considerably lower, resulting in a 4-fold improvement in signal-to-noise compared to Sephacryl TM dextran beads.

We claim:

1. Polyacrylamide supports to which RNA or DNA oligonucleotides are covalently attached via a thioether linkage, wherein:
   at least about 95% of the oligonucleotides are linked to the carboxamide side groups of the support at the 5'-ends of the oligonucleotides;
   the polyacrylamide supports have a molecular weight exclusion limit of at least about $2 \times 10^7$ daltons; and
   the supports to which the oligonucleotides are covalently attached via a thioether linkage are selected from the group consisting of supports represented by the formulae:

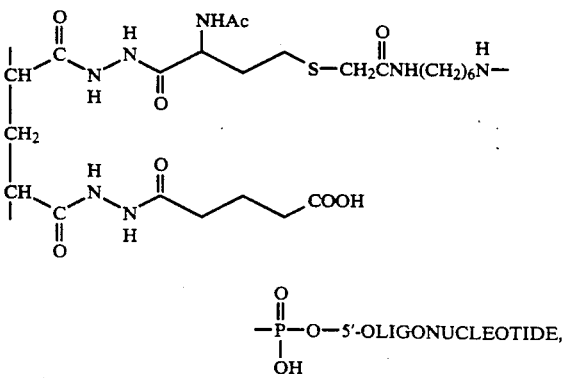

-continued

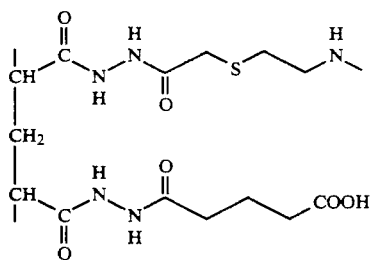

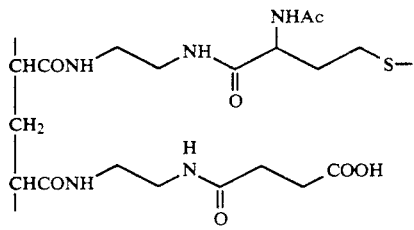

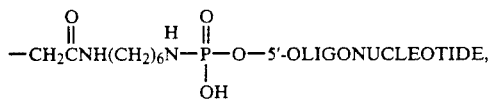

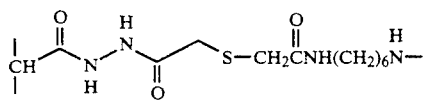

-continued

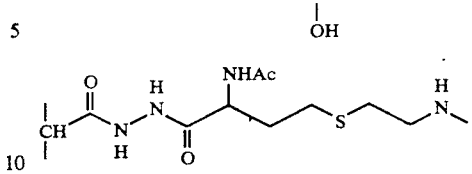

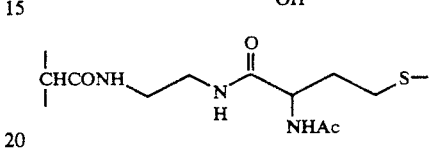

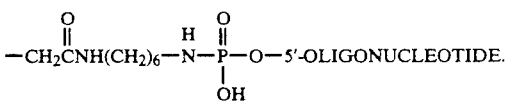

2. The supports of claim 1 wherein the repeating units each contain three hydroxymethyl groups and one secondary amide group.

3. The supports of claim 1 wherein the oligonucleotides are about 12 to 200 nucleotides in length.

4. The supports of claim 1 wherein the oligonucleotides are about 15–40 nucleotides in length.

5. Oligonucleotides derivatized at their 5'-terminal phosphate group with bromoacetyl group and having the following formula:

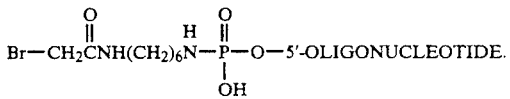

* * * * *